United States Patent
Okada (10) Patent No.: US 10,272,254 B2
(45) Date of Patent: *Apr. 30, 2019

(54) CURRENT DIVERTER FOR MAGNETIC STIMULATION OF BIOLOGICAL SYSTEMS

(71) Applicant: MOMENT TECHNOLOGIES, LLC, Brookline, MA (US)

(72) Inventor: Yoshio Okada, Brookline, MA (US)

(73) Assignee: MOMENT TECHNOLOGIES, LLC, Brookline, MA (US)

( * ) Notice: Subject to any disclaimer, the term of this patent is extended or adjusted under 35 U.S.C. 154(b) by 657 days.

This patent is subject to a terminal disclaimer.

(21) Appl. No.: 14/701,334

(22) Filed: Apr. 30, 2015

(65) Prior Publication Data

US 2015/0231405 A1  Aug. 20, 2015

Related U.S. Application Data

(60) Division of application No. 13/937,119, filed on Jul. 8, 2013, now Pat. No. 9,026,194, which is a continuation-in-part of application No. 13/040,027, filed on Mar. 3, 2011, now Pat. No. 8,483,795.

(51) Int. Cl.
| | |
|---|---|
| *A61N 2/00* | (2006.01) |
| *A61N 1/44* | (2006.01) |
| *A61N 2/02* | (2006.01) |
| *A61B 5/04* | (2006.01) |
| *G01R 33/035* | (2006.01) |

(52) U.S. Cl.
CPC .......... *A61N 2/002* (2013.01); *A61B 5/04008* (2013.01); *A61N 1/445* (2013.01); *A61N 2/006* (2013.01); *A61N 2/02* (2013.01); *G01R 33/035* (2013.01); *G01R 33/0354* (2013.01); *A61B 2562/14* (2013.01)

(58) Field of Classification Search
None
See application file for complete search history.

(56) References Cited

U.S. PATENT DOCUMENTS

| | | |
|---|---|---|
| 5,494,033 A | 2/1996 | Buchanan et al. |
| 5,938,598 A | 8/1999 | Takeda et al. |
| 6,226,538 B1 | 5/2001 | Kugai et al. |
| 6,815,949 B2 | 11/2004 | Kandori et al. |
| 7,002,341 B2 | 2/2006 | Baudenbacher et al. |
| 7,197,352 B2 | 3/2007 | Gott et al. |
| 7,262,597 B2 | 8/2007 | Woods et al. |
| 7,403,809 B2 | 7/2008 | Tsukada et al. |
| 7,589,525 B2 | 9/2009 | Woodard et al. |
| 7,672,707 B2 | 3/2010 | Takeda |
| 7,729,740 B2 | 6/2010 | Kraus, Jr. et al. |
| 7,756,564 B2 | 7/2010 | Matsui et al. |

(Continued)

OTHER PUBLICATIONS

International Search Report, dated Sep. 26, 2012 (PCT/US2012/026476), 3 pages.

(Continued)

*Primary Examiner* — Katherine L Fernandez
*Assistant Examiner* — Michael S Kellogg
(74) *Attorney, Agent, or Firm* — The Maxham Firm; Lawrence Maxham (57) ABSTRACT

Apparatus and methods which enable the stimulation of neurons oriented in all directions within a biological structure using applied magnetic fields.

11 Claims, 7 Drawing Sheets

(56) References Cited

U.S. PATENT DOCUMENTS

2007/0239059 A1 10/2007 McIver
2013/0038325 A1* 2/2013 Okada ............... G01R 33/0354
 324/248

OTHER PUBLICATIONS

D. Cohen et al., "Magnetic Field Produced by a Current Dipole," J. Electrocardiology, 9 (4), pp. 409-417 (1976).
F. Grynszpan et al., "Model Studies of the Magnetogardiogram," Biophysical Journal, vol. 13, pp. 911-925 (1973).
Y. Okada et al., "Magnetic Evoked Field Associated With Transcortical Currents in Turtle Cerebellum," Biophys. J., vol. 53, pp. 723-731 (1988).
R. Plonsey, "Generation of Magnetic Fields by the Human Body (Theory)," Biomagnetism, Berlin, De Gruyter, pp. 177-205 (1981).
J. Malmivuo et al., Bioelectromagnetism, "Principles and Applications of Bioelectric and Biomagnetic Fields," "Magnetic Stimulation of Neural Tissue," Oxford University Press, 10 pages (1995).
R. J. Charles, "Structural State and Diffusion in a Silicate Glass," Journal of the American Ceramic Society, vol. 45, No. 3, pp. 105-113 (1962).
P.W. May, "CVD Diamond—a new Technology for the Future?" Endeavour Magazine 19(3), 8 pages, (1995).
Sternickel et al., Biomagnetism using SQUIDs: status and perspectives, Supercond. Sci. Technol 19, pp. 160-171 (Feb. 15, 2006).
J.R. Taylor, "An Introduction to Error Analysis: The Study of Uncertainties in Physical Measurements," (1.6 Estimating Uncertainties in Repeatable Measurements) Physics—chemistry—engineering, A series of books in physics, Edition 2, p. 10, Publisher University Science Books, 1997 ISBN 093570275X, 9780935702750.
R. Pethig et al., The passive electrical properties of biological systems: their significance in physiology,biophysics and biotechnology Institute of Molecular and Biomolecular Electronics, University College of North Wales, Phys. Med. Bioi., vol. 32, No. 8, 933-970 (1987).
P. Tallgrena et al., "Evaluation of commercially available electrodes and gels for recording of slow EEG potentials," Department of Biological and Environmental Sciences, University of Helsinki, Finland. Department of Clinical Neurophysiology. Clinical Neurophysiology 116 (2005) 799-806.

* cited by examiner

CURRENT DIVERTER FOR MAGNETIC STIMULATION OF BIOLOGICAL SYSTEMS

CROSS-REFERENCE TO PRIOR APPLICATIONS

The present application is a divisional application of application Ser. No. 13/937,119, filed 8 Jul. 2013, now U.S. Pat. No. 9,026,194, issued 5 May 2015, which is a continuation-in-part of application Ser. No. 13/040,027, filed 3 Mar. 2011, now U.S. Pat. No. 8,483,795, issued 9 Jul. 2013, which are both hereby incorporated by reference in their entireties.

FIELD OF THE INVENTION

The present application relates generally to the field of measuring the magnetic fields produced by naturally occurring electric currents which flow in the brain and other organs of humans and animals, in tissue slices and cultures made from these organs, in cells harvested from these tissues, and more particularly to the apparatus and methods for making such measurements. It farther relates generally to the use of magnetic induction to produce electrical currents in the brain and other organs of humans and animals and in biologic tissue slices and cultures.

BACKGROUND OF THE INVENTION

The term magnetoencephalography (often, abbreviated by the acronym "MEG") refers to the detection and measurement of the magnetic fields, which are produced by the electric currents, which flow naturally within the bodies of humans and animals. For example, such electric current flows are a fundamental feature of the functioning of the neurological system of a human being. Charged ionic flows within the neurons, which make up part of the human brain are, in effect, an electric current, which, produces a magnetic field, which can be measured using the methods of MEG. The electric currents, which drive the pumping of the heart in an animal, produce magnetic fields, which can be measured using magnetocardiography. Measurements of the magnetic fields produced by these electric currents can be used to deduce information about the size and direction of the currents as a function of time as well as their location and distribution within the body of a person, and therefore to provide information about the state of health and the state of function of the person.

Apparatus and methods of MEG have been developed and expanded over the past forty years, enhancing sensitivity to enable the detection of magnetic fields produced by electric currents flowing deep within the body. The "field of view" of the magnetometers used for MEG have been systematically expanded from single channel detectors of the magnetic field at one location to large helmet-shaped systems measuring the values of the magnetic fields at up to 275 locations around the head of a human being or up to 150 locations over the chest of a human being.

Magnetoencephalography has also been used to measure magnetic fields produced by electric currents flowing in biologic samples such as brain tissue slices of laboratory animals. In these systems, methods have been developed to bring the detector of the magnetic field as close as possible to the electric current itself to maximize the size of the measured signal and the ratio of the signal to the background magnetic noise. In some case, spacing as small as 1 mm or less has been achieved.

Generally, the biomagnetic measurements of biogenic electric currents are useful for measuring the distribution of such currents in a tissue such as a brain slice or in an organ such as a brain or heart.

One major limitation in the application of the biomagnetic techniques for the purposes outlined above arises from a fundamental property of magnetic fields produced by electric currents flowing in tissues or organs. Any such tissues or organs can be described by a circuit of electrically active cells that produce the biogenic current. In intact humans or animals the tissue of the organ that contains such electrogenic cells is saturated with physiological saline. In in vitro preparations, such a tissue is immersed in a bath of physiological saline. The physiological saline conducts electricity; thus, the medium containing the saline such as the brain or the head, or a bath containing the tissue, is called "conductive medium." From the fundamental principles governing electromagnetism in conductive media, an electric current which flows within and proximate to the surface of such a conductive medium and flows in a direction which is perpendicular to the surface of that medium produces no net magnetic field external to the medium itself. This is strictly true when the conducting medium is spherical or flat. A large bath can be thought of as a part of an infinitely large sphere. But, it is very well approximated even in a conducting medium that lacks a spherical symmetry when the cells are close to the boundary separating the conducting medium from the surrounding non-conducting medium. This factor has limited the utility of biomagnetic measurements such as MEG in providing complete information about electric currents in a tissue or in an organ. The conventional biomagnetic techniques can provide the information only about those components of the electric currents flowing within conducting media, which flow in a direction parallel to the surface of that medium, but not the currents, which flow normal to the surface. In particular, this factor has impacted heavily on the application of MEG to examine the brains of prematurely born human babies, since in these babies the cerebral cortex is poorly developed and larger percentages of neuronal activity are perpendicular to the surface of the skull and cannot be easily detected with conventional biomagnetic techniques. In general, this factor has significantly constrained the application of the biomagnetic techniques for measuring biogenic currents from human and animal brains.

The term transcranial magnetic stimulation (often abbreviated by the acronym "TMS") refers to the process of applying a pulse of magnetic field to the brain of an animal or human being in order to stimulate the neurons within the brain. The technology of TMS is now well known and the procedure of TMS is routinely used for both research and clinical purposes. A summary of current methods is given in chapter 22 of the text *Bioelectromagnetism*, authored by J. Malmivuo and R Plonsey, published by the Oxford University Press in 1995.

All of the current TMS methods utilize electrical coils placed on or adjacent to the head of the subject to produce a magnetic field within the brain when a pulse of electrical current is sent through the coils. Generally, TMS coils are constructed in a planar format and placed as close to the head as practical to maximize the strength of the magnetic field within the head, and hence the corresponding induced stimulating electric field. The pulsed magnetic field produced by such coils typically has a direction, which is perpendicular to the plane of the coils and to the adjacent surface of the head. This pulsed field then induces a pulsed electric field within the head and within the brain, which is oriented orthogonal to the direction of the pulsed magnetic field. The pulsed electric field then stimulates primarily those neurons within the structure of the brain, which are parallel to the induced electric field.

The brain comprises a complex structure with many folds and convex as well as concave surfaces. The cortex of the brain contains large numbers of pyramidal neurons, which line the surfaces. An electric field applied in a direction parallel to a neuron, if sufficiently strong, can cause that neuron to 'fire' or activate. However, the same electric field applied in a direction orthogonal to a neuron will generally not result in activation. Thus the current methods and apparatus used for TMS of the brain only stimulate a portion of all of the neurons within the brain, namely the neurons with an orientation parallel to the nearby surface of the head. There is a need to find a way to stimulate those neurons, which are oriented perpendicular to the surface of the head

SUMMARY OF EMBODIMENTS OF THE INVENTION

Accordingly, it is a purpose of embodiments of the present invention to provide apparatus and methods for enabling the detection and assessment of all components of the biogenic currents, including the electric current flowing in a conductive medium in a direction perpendicular to the boundary surface separating a conducting medium (for example, a head or a saline bath) from the non-conducting medium, (for example, air) by means of a magnetometer located outside of the medium itself. The use of these embodiments will therefore enable a more complete assessment of all components of electric currents, which flow within a conductive medium.

It is a further purpose of certain embodiments of the present invention to provide apparatus and methods for enabling the electromagnetic stimulation of neurons of all directional orientations within the brain of a human being. It is a further purpose of those embodiments disclosed to enable the electromagnetic stimulation of the neurons of all directional orientations in samples of tissue containing such neurons in a laboratory to enable the more efficient and effective study of the characteristics and requirements for neuronal activation in vitro.

The following summary of embodiments of the invention is provided to enable an understanding of some of its novel features but is not intended to be a full description. A full appreciation of the aspects of the various embodiments will be provided by the specification, claims, drawings, and abstract as a whole.

One feature of the invention is to provide a structure, which provides a secondary source of magnetic field, which is induced by and reflects a primary electric current flowing in a conductive medium. Detection and measurement of the magnetic field produced by the secondary source will provide information about the size and location of the primary electric current that is oriented perpendicular to the boundary surface separating the conducting medium from the non-conducting medium (such as air). Here, the primary current source of biomagnetic field is a cell or a group of cells that produce the electric current, and a secondary current source is a source of magnetic field in the conducting medium produced by the primary source. The secondary source in general exists at boundary surfaces separating regions differing in electrical conductivity. Secondary sources generate magnetic fields that are directly related to the current in the primary source. Thus, it is possible to indirectly measure the primary current perpendicular to the boundary surface, which is otherwise not detectable with conventional biomagnetometry.

A further feature of the invention is to provide an apparatus and method, which enables an expanded capability to detect and assess electric currents flowing within the brain and body of human beings and animals.

A further feature of the invention is to provide an apparatus and method, which enables an expanded capability to detect and measure electric currents flowing in specimens of neurological tissue from humans and animals where such measurements are conducted on the specimens in vitro.

A further feature of the invention is to provide an apparatus and method, which enables an expanded capability to perform functional assessments of the brains of neonates and other very young human beings by means of MEG.

One feature of those embodiments intended for use with TMS is the provision of a structure, which enables the use of magnetic field generating coils placed near a portion of the surface of the head of a human being to stimulate neurons of all directional orientations within the brain of the human being.

A further feature of these embodiments is the enablement of multiple foci of stimulation in the brain of a human being or other animal.

A further feature of these embodiments is to provide a laboratory apparatus, which enables the study by means of magnetic stimulation of the electrophysiology of groups of neuron cells within tissue samples, immersed in an electrically conductive medium such as saline solution.

A further feature of these embodiments is to provide a unitary apparatus, which provides a plurality of stimulation sources and a conductive medium in a modular form, which can easily be placed over areas of the surface of a human or animal body in a variety of configurations.

BRIEF DESCRIPTION OF THE DRAWING

The objects, advantages, features, and other desirable characteristics of embodiments of the invention can be readily perceived from the following detailed description and attached drawing, in which.

DETAILED DESCRIPTION OF EMBODIMENTS OF THE INVENTION

It is a fundamental property of the physics of electromagnetism that, at the boundary between a conductive medium and a non-conductive medium, an electric current which is flowing within the conductive medium and in a direction parallel to the boundary produces a magnetic field that extends throughout both the conductive and non-conductive media. However, an electric current, which is flowing within the conductive medium and in a direction orthogonal to the boundary, produces a magnetic field, which extends throughout the conductive medium but produces no magnetic field in the non-conductive medium. This is strictly true for a conducting medium having a spherical symmetry such a sphere or a semi-infinitely large saline bath. The human head is nearly spherical, at least over a large dorsal portion of the head. A large bath containing a tissue immersed in a physiological saline approximates an infinitely large bath. In these eases the approximation is excellent (see F. Grynszpan and D. B. Geselowitz, Biophysics Journal, Vol 13, pp. 911-925 (1973); also D. Cohen and H. Hosaka, J. Electrocardiol., 1976, Vol. 9, pp, 409-417 (1976); also Y. C. Okada and C, Nicholson, Biophys. J., Vol. 53, pp. 723-731 (1988)).

One effective means for determining the characteristics of an electric current flowing in a conductive medium—location, amplitude, direction of flow as a function of time—is by measuring the magnetic field produced by that current. However, because magnetic fields external to the conductive medium are only produced by those currents which flow in a direction parallel to the surface or boundary of the medium, this method is strongly limited. Placing a magnetic field detector within the conductive medium itself is a potential approach but faces numerous practical difficulties. Placing a magnetic field detector external to the conductive medium limits this method to determining the characteristics only for the electric current components, which are parallel to the surface of the medium.

Figure 1:
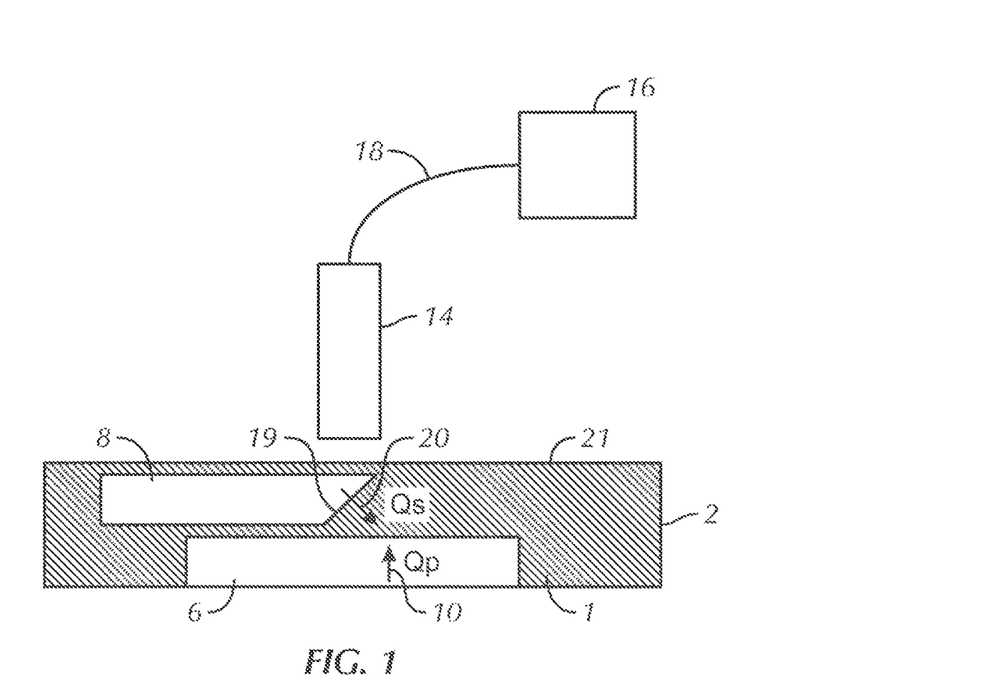
FIG. 1 is a schematic view of an apparatus which enables the detection and measurement of the magnetic field produced by electric currents flowing in a biologic sample located in a conductive material (for example, a liquid or a gel) in accordance with an embodiment of the invention.

Many embodiments of the current invention are aimed at alleviating this limitation. In FIG. 1, a biologic sample 6 is shown immersed in a conductive solution 1 contained within a vessel 2. A preferred embodiment would use a saline solution as a conductive solution. An alternative could use an agar soaked with physiological saline. Small electric current elements flowing within the biologic sample can be represented as "current dipoles," each of which is characterized by a current amplitude and direction of flow and a length between a source and a sink between which the current flows. For example, if the biologic sample were a slice of brain tissue containing a neuron, the functioning of that neuron could be characterized by an electric current flowing through the neuron, and the "equivalent current dipole" representation of that functioning would include the spatial position and orientation of the neuron and the current amplitude between a source and a sink in the neuron. In the biologic sample in FIG. 1, an equivalent primary current dipole in a population of vertically oriented neurons is represented by arrow 10. Any current dipole within the sample can be expressed by basic vector mathematics as the sum of two components, one component oriented along the direction perpendicular to the surface of the sample and one component oriented in a direction parallel to the surface of the sample. In FIG. 1, current dipole $Q_P$ 10 is oriented perpendicularly to the surface of biologic sample 6. Placed above the top surface of the biologic sample and within conductive medium 1 is non-conductive solid 8 having flat face 19 at one end. In a preferred embodiment, the non-conductive solid is cylindrical in cross-section and has a face at one end, which is flat and at an angle approximately 45 degrees from being parallel with the upper surface of the sample. The 45 degree face is positioned approximately above primary current dipole 10. A preferred material for the non-conductive solid is glass. Alternative materials from which the non-conductive solid can be fabricated include, but are not limited to, sapphire, quartz, diamond, and filled composite plastics.

Figure 2:
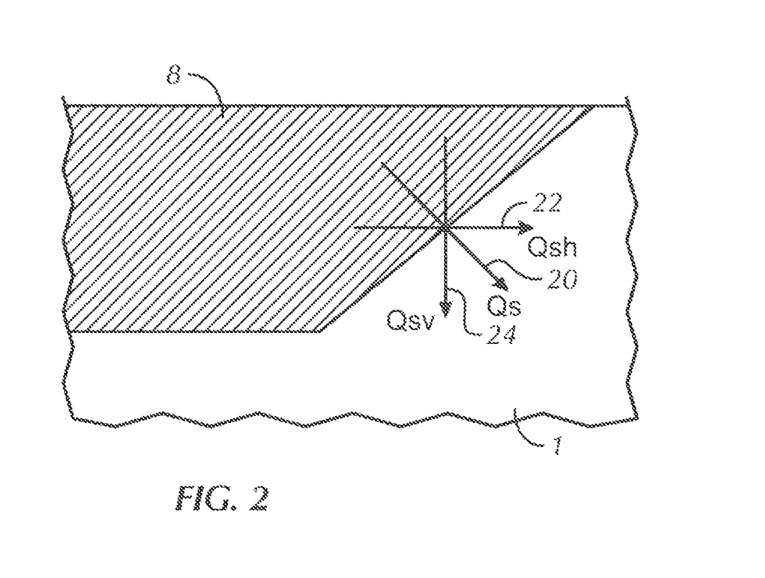
FIG. 2 is an enlarged schematic view of the non-conductive structure of FIG. 1 in which a secondary source is induced by a primary electric current.

According to the theory of secondary sources in conductive and non-conductive media, a secondary source of magnetic field $Q_S$ 20 is induced on surface 19 of the non-conductive solid by primary current dipole 10 (see, for example, R. Plonsey in *Biomagnetism*, Berlin, De Gruyter, pp. 177-205 (1981)). This secondary dipolar source is positioned on the boundary surface of the non-conductive solid oriented perpendicular to face 19 of the non-conductive solid. Surface 19 may be referred to as a primary source mirror or PRISM. FIG. 2 shows a fragment of non-conductive solid 8 and secondary source 20 induced by primary current 10. Secondary source 20 can be resolved into two components by simple vector physics, one component, represented by arrow 22, being parallel and the other component, represented by arrow 24, being perpendicular to surface 21 of conducting medium 1 in FIG. 1. Since component 22 is parallel to surface 21, it produces a net magnetic field above the conductive medium, which can be detected and measured by a magnetic field sensor or magnetometer 14. The output, from magnetometer 14 is transmitted to a data acquisition and analysis system 16 via cable 18. This apparatus then produces values of the magnetic field produced by secondary source magnetic field 20, which is induced by primary current dipole 10. This value provides information, such as location and current amplitude as a function of time, characterizing the primary current. As the primary current changes its amplitude in time, the values of the magnetic field will change as well. Frequency response available via this method utilizing secondary sources will be comparable to the frequencies exhibited by the primary current. Tire position of the non-conductive solid can be changed to provide additional information about primary current 10 such as the volume of the active tissue in sample 6.

A typical apparatus such as that described above for use in a biomagnetic application would consist of: 1) vessel 2, which may be a petri dish with diameter of approximately 5 cm and depth of about 5 mm; 2) biologic sample 6 having thickness of about 0.01 to 0.4 mm: 3) an oxygenated physiological saline solution as a conductive medium filling the petri dish to the rim; 4) a cylindrical glass rod of diameter approximately 1 mm and length of about 2 mm as the non-conductive solid 8 with one end sealed and polished to form surface 19 (PRISM) at an angle of approximately 45 degrees from the axis of the cylindrical glass rod; and 5) wherein magnetometer 14 has a sensitivity to magnetic fields of at least 100 femtoTesla per root Hertz. However, a variety of types of magnetometers may be used to detect the magnetic field produced by one or more secondary sources, depending on the strength of the secondary source. Hall effect magnetometers, flux gate magnetometers, pumped optical or atomic magnetometers, and SQUID-based magnetometers, amongst others, are all candidates for use in this apparatus.

Figure 3:
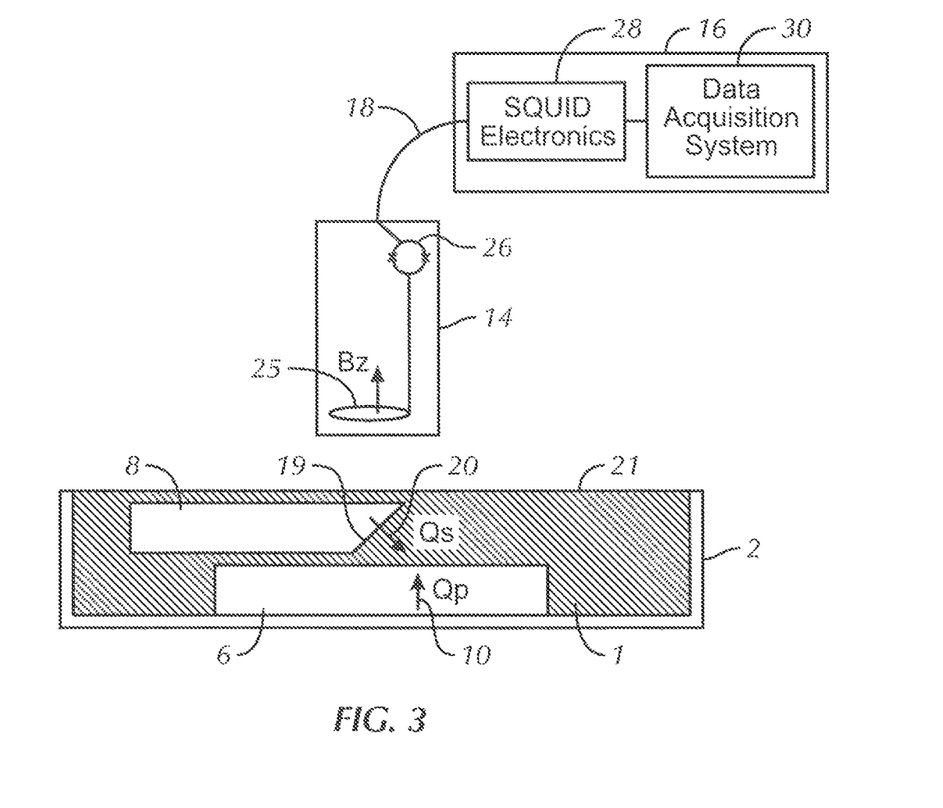
FIG. 3 is a schematic diagram of the apparatus of FIG. 1 wherein the magnetic fields are detected and measured by means of a superconducting magnetometer, in accordance with an embodiment of the invention.

A preferred embodiment of the configuration illustrated in the foregoing is shown, in FIG. 3. In this figure, magnetometer 14 is a superconducting magnetometer, which utilizes a superconducting quantum interference device or SQUID to provide a greater sensitivity to the magnetic fields than other types of magnetometers. This type of magnetometer is well known. See, for example, Tsukada et al., U.S. Pat. No. 7,403,809, which discloses a magnetometer of this type. In this embodiment, the magnetic field produced by secondary source 20 induces a current in pickup coil 25 located within the magnetometer 14. That current is coupled to SQUID device 26 within the magnetometer. The output of the SQUID device, which is a measure of the magnetic field produced by the secondary source, is transmitted via cable 18 to SQUID electronics 28 and data acquisition system 30 in data acquisition and analysis system 16.

The embodiment shown in FIG. 3 and described above is a preferred embodiment for measuring electric currents flowing in tissue samples, which lend themselves to immersion in a conductive bath.

Figure 4:
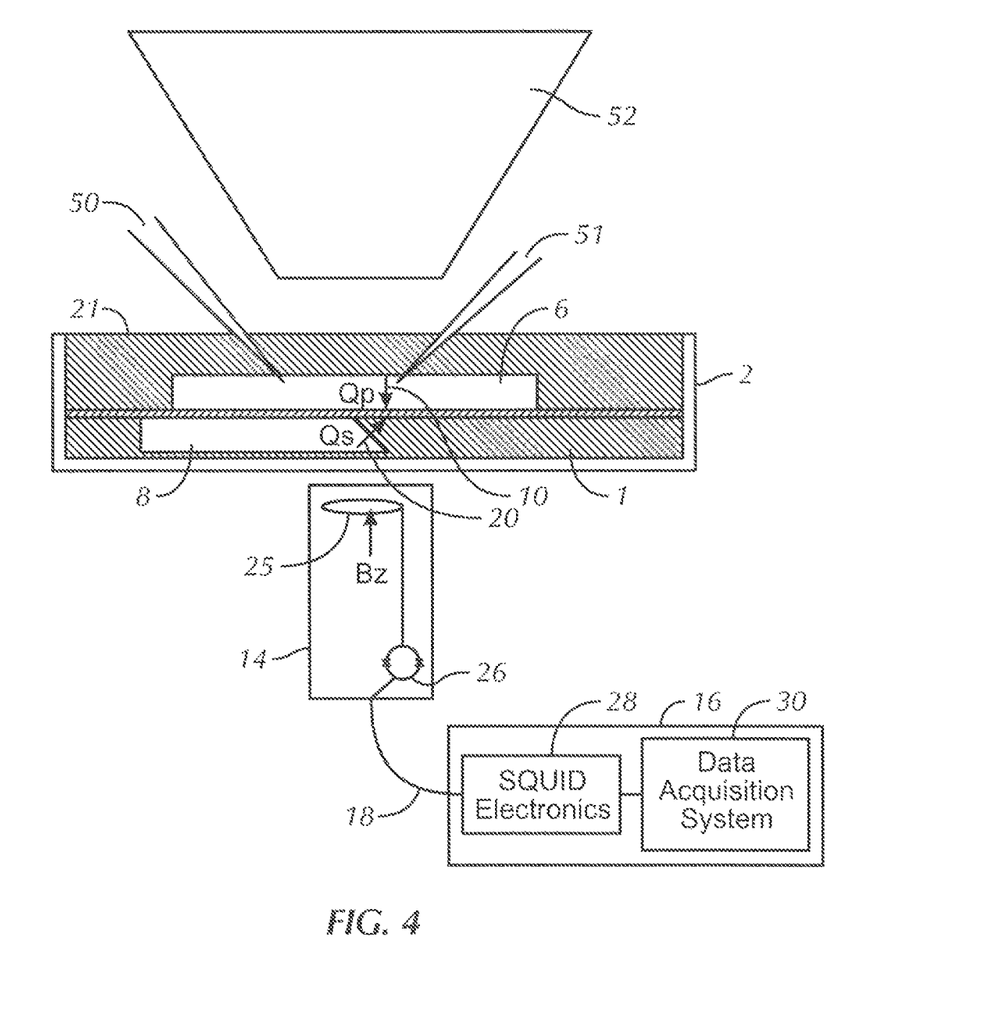
FIG. 4 is a schematic view of the apparatus of FIG. 1 in which the magnetic fields are detected and measured by means of a superconducting magnetometer located below the sample with a conventional optical microscope above the sample to visualize the sample, in accordance with an embodiment of the invention.

Another preferred embodiment of the configuration of FIG. 1 is shown in FIG. 4. In this figure, secondary source 20 in non-conducting solid 8 is produced by primary source 10 in tissue sample 6. All of these structures are immersed in conducting medium 1 in vessel 2 having a boundary surface 21 separating the conducting medium from the non-conductive medium (air). Unlike the previous preferred embodiment shown in FIG. 3, this embodiment makes it possible to measure the magnetic field from the otherwise non-detectable primary source 10 using the magnetometer located below the sample and at the same time visualize the entire tissue sample with conventional optical microscope 52 from above. The neurons in the sample can be stimulated with one or more stimulating electrodes 50. Electrical activity in an individual neuron or a population of neurons can be directly measured with one or more recording electrodes 51, which measure the potentials resulting from the neuronal activity. This configuration increases the versatility and applications of the invention.

The two embodiments in FIG. 3 and FIG. 4 feature a single magnetometer 14. An expanded apparatus can include a large number of magnetometers, which can simultaneously detect and measure the magnetic field at many positions produced by a secondary source induced by one primary source. Another expanded embodiment can include multiple non-conductive solids in which secondary sources can be induced by multiple primary sources, with the magnetic fields from all of the secondary sources being detected and measured by all of the multiple magnetometer detector channels.

Figure 5:
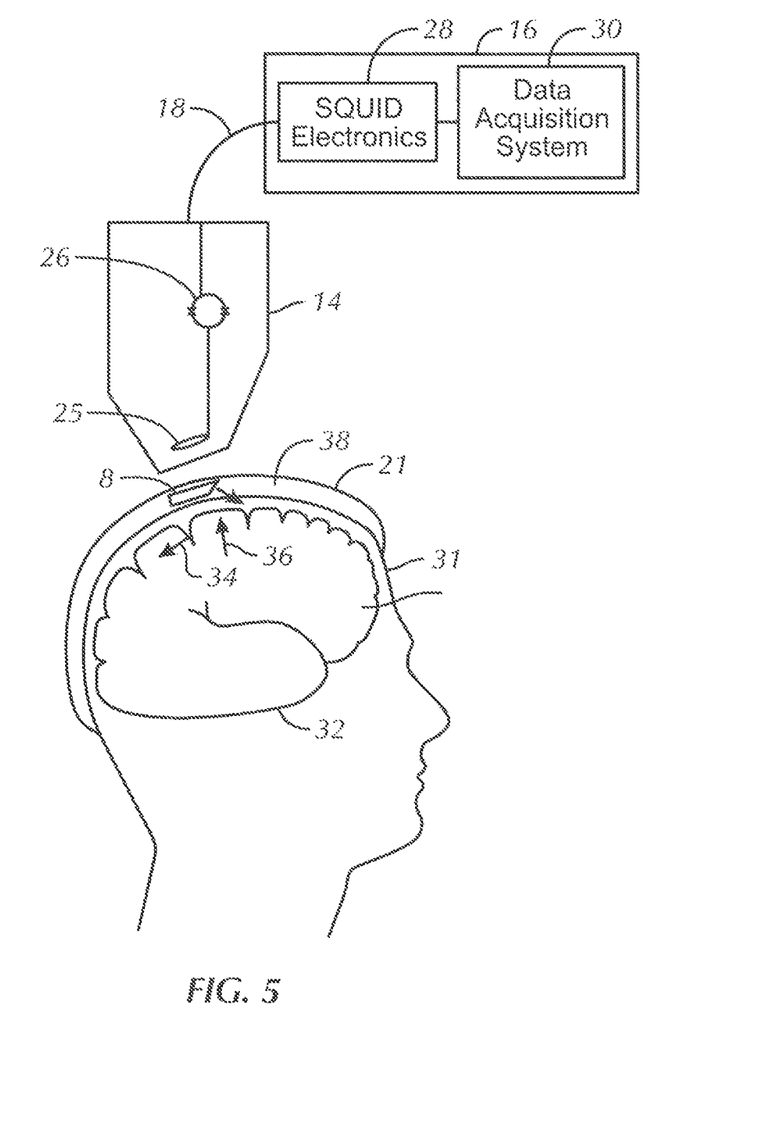
FIG. 5 is a schematic view of an apparatus, which enables the enhanced detection of electric currents flowing in the brain of a human being, in accordance with an embodiment of the invention.

The apparatus described above can also be configured with a variety of alternative geometries to suit various applications. The same principles, which underlie the embodiments described in detail above, will apply, for example, to enhance the ability to measure electric currents flowing within the body of animals or human beings. FIG. 5 shows such an embodiment, which is suitable for measuring the electric currents flowing within the brain 32 of a human being. Large portions of the human brain and head can be modeled as a set of concentric spheres. (See, for example, F. Grynszpan and D. B. Geselowitz, *Model Studies for the Magnetocardiogram*, Biophysics Journal Vol. 13, pp. 911-925 (1973)). The brain itself is a conductive medium containing neuronal structures, which carry electric currents. The brain is immersed in the conductive cerebral spinal fluid. The brain is surrounded by the dura, then the skull, and finally the scalp. The last three layers are poor but non-zero conductors. Thus, some currents in the brain, for example, the primary current dipole 36 produced by neurons in the gyrii of the cortex, are oriented perpendicular to the overlying boundary surface separating the head from air. Other currents are oriented tangential to the overlying boundary surface (for example, primary current dipole 34). Conventional magnetoencephalography can measure the magnetic field only from tangential currents such as 34, but not the magnetic held from radial currents such as 36. The invention embodied in FIG. 5 circumvents this fundamental limitation and makes it possible to detect the magnetic field, from radial currents 36. In FIG. 5, a conductive gel 38 is spread over the skull, providing another layer of conductive medium. A preferred conductive gel is electroencephalography (EEG) electrode paste. A non-conductive solid 8 of generally cylindrical cross-section and having a flat surface at one end, the plane of which is at an angle of approximately 45 degrees to a plane tangent to the inner surface of the skull, is immersed in the conductive gel. Following the same principles described above, radially oriented primary currents in the brain located close to the PRISM do not produce a magnetic field external to the skull but do induce a secondary source in the PRISM. That secondary source produces a magnetic field which can be detected and measured by magnetometer 14, using the magnetic field detection coil 25 coupled to SQUID 26 which is controlled by SQUID electronics 28, whose output is connected to data acquisition system 30 in box 16. This apparatus in tins way enables the detection and measurement of a greater amount of brain electrical activity than is otherwise possible.

The embodiment of FIG. 5 has particular use for examining the brain activity of very young children since, due to poorly developed cortical folding in very premature brains, the brain in the early stages of development contains greater percentages of activity with electric currents flowing in a direction perpendicular to the surface of the skull than in more developed brains. This embodiment is also adapted for when studying the brains of animals with brains containing few sulci and for which most neuronal electrical current flows are perpendicular to the animal's skull.

Figure 6:
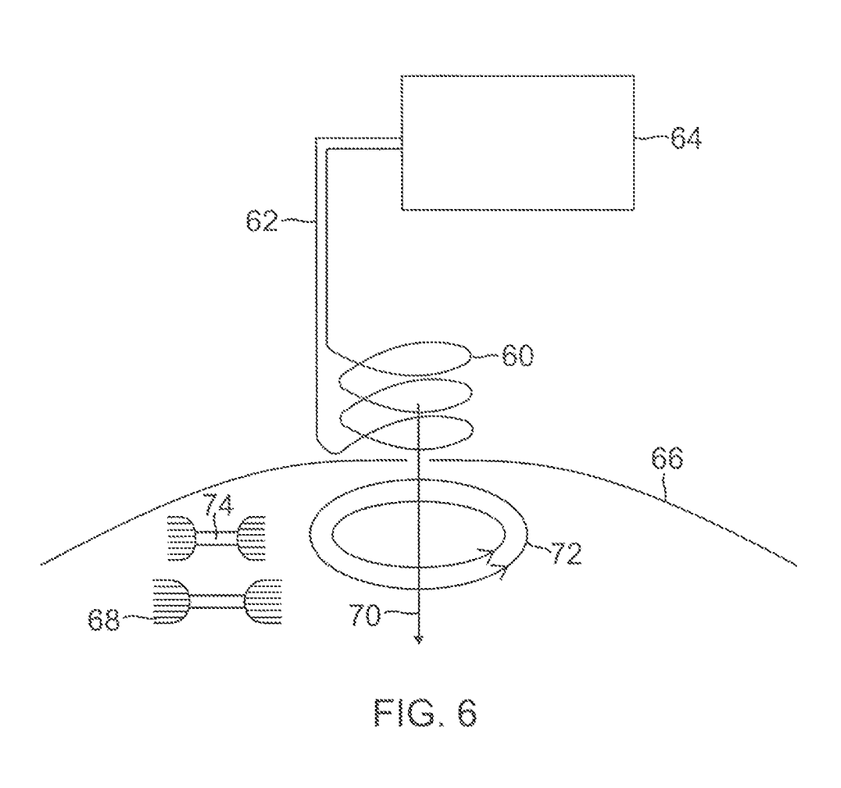
FIG. 6 is a schematic view of a prior art transcranial magnetic stimulation apparatus as currently employed, shown in relation to a portion of a human head.

FIG. 6 shows a typical currently used apparatus for transcranial magnetic stimulation ("TMS") of neurons within the head 66 of a human being. Pulses of electrical current are directed through planar electrical coil 60 from current source 64 via connection wires 62. The plane of the electrical coil is parallel to the surface of the head. Examples of appropriate electrical current sources are presented in Chapter 22 of Bioelectromagnetism, authored by J. Malmivuo and R Plonsey, cited above. The pulses of electrical current produce a magnetic field pulse 70, which is oriented parallel to the axis of coil 60 and thus perpendicular to the surface of the head. The interior of the head is comprised of conductive media, including neural tissue making up the brain and cerebral spinal fluid. Therefore, the magnetic field pulse induces a pulse of electrical voltage and consequent electrical current 72 oriented perpendicular to the direction of the magnetic field pulse and thus parallel to the surface of the head adjacent to the coil. This voltage and current pulse in turn creates a polarizing or activating voltage pulse in neurons 74 which are oriented parallel to them. However, no polarizing effect is realized in those neurons which are not oriented parallel to the applied pulse.

Figure 7:
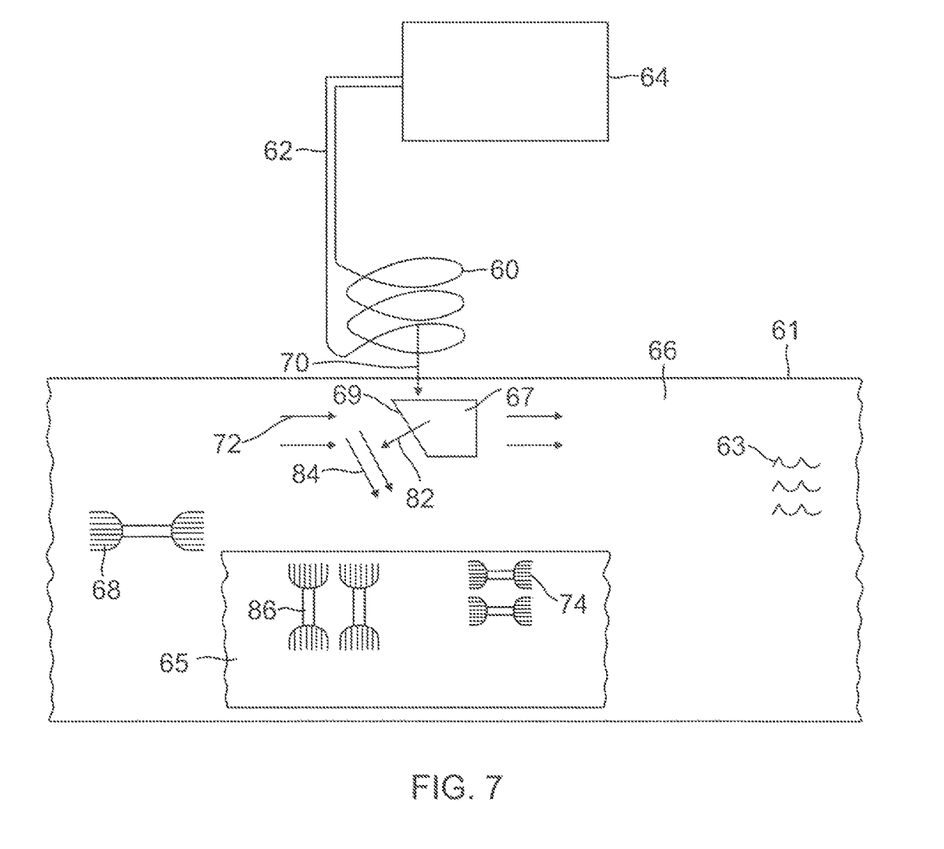
FIG. 7 is a cross sectional view of an embodiment of the invention when used with a neuronal tissue sample immersed in a saline-filled dish.

FIG. 7 shows an embodiment of the current invention, which can induce polarization in those neurons not otherwise stimulated by the known apparatus in FIG. 6. In this illustration, the embodiment is employed to stimulate neurons within neuronal tissue sample 65, which is immersed in conductive saline solution 63 within laboratory dish 61. As in the prior art apparatus shown in FIG. 6, an electric current pulse generated from current source 64 is applied via connecting wires 62 to planar electrical coil 60 to produce a magnetic field pulse 70. The planar coil is oriented parallel to the surface of the saline solution, and the magnetic field produced is thus oriented perpendicular to that surface. This magnetic field pulse induces a voltage pulse and resultant electrical current pulse to flow within the saline solution and within the tissue sample in accord with Lenz's Law of basic electromagnetism, with those currents flowing in a direction parallel to the surface of the saline. As with the prior art apparatus, this current pulse can directly stimulate and induce polarization and depolarization activity in neurons 74 which are themselves oriented parallel to the direction of the current flow. In this embodiment, however, a non-conductive solid object 67 (referred to hereafter as a "KEEL") is positioned within the saline and between the tissue sample and the electrical coil.

The non-conductive solid object has at least one planar surface 69 which is oriented at an angle which is neither parallel to nor perpendicular to the surface of the saline. KEEL 67 serves to divert a portion of the electrical current pulse flowing within the saline so that the diverted current flows along the at least one planar surface 69. The means for this diversion can be understood in terms of the theory of secondary sources discussed above. The magnetic field pulse produced by electrical coil 60 produces secondary source or secondary source pulse 82 at surface 69 of the KEEL. This secondary source pulse induces the flow of electrical current parallel to surface 69. The current flow arising from the secondary source adds to the primary current flow produced by electrical coil 60. The sum of the two current pulses makes up diverted current pulse 84. The diverted current pulse may be resolved into one component flowing parallel to and one component flowing orthogonal to the surface of the saline. The component of the current pulse which is flowing in a direction orthogonal to the surface of the saline will serve to stimulate those neurons 86 within the tissue sample which are oriented parallel to this component of the current pulse, neurons which are not otherwise stimulated by the prior art apparatus.

A preferred embodiment for a KEEL would have the non-conductive solid object to be cylindrical in cross-section and have a face at one end which is flat and at an angle approximately 45 degrees from being parallel with the upper surface of the saline. The 45-degree face is positioned approximately below the axis of electrical coil 60. However, since the purpose of the non-conducting solid object in this embodiment is to simply divert the electrical current pulses so that a portion of the current pulse flows in a direction perpendicular to the surface of the saline, a wide variety of shapes for the non-conductive solid object may be employed. Similarly, a wide variety of dimensions for the non-conductive solid object may be employed, provided the object can be positioned within the saline and between the tissue sample and the saline surface. While a preferred material for the non-conductive solid is glass, alternative materials from which the non-conductive solid can be fabricated include, but are not limited to, sapphire, quartz, diamond, and filled composite plastics. Furthermore, while a simple planar electrical coil is described herein for illustration of the principle of operation of a KEEL, many different forms of electrical coils may be employed in this embodiment.

Figure 8:
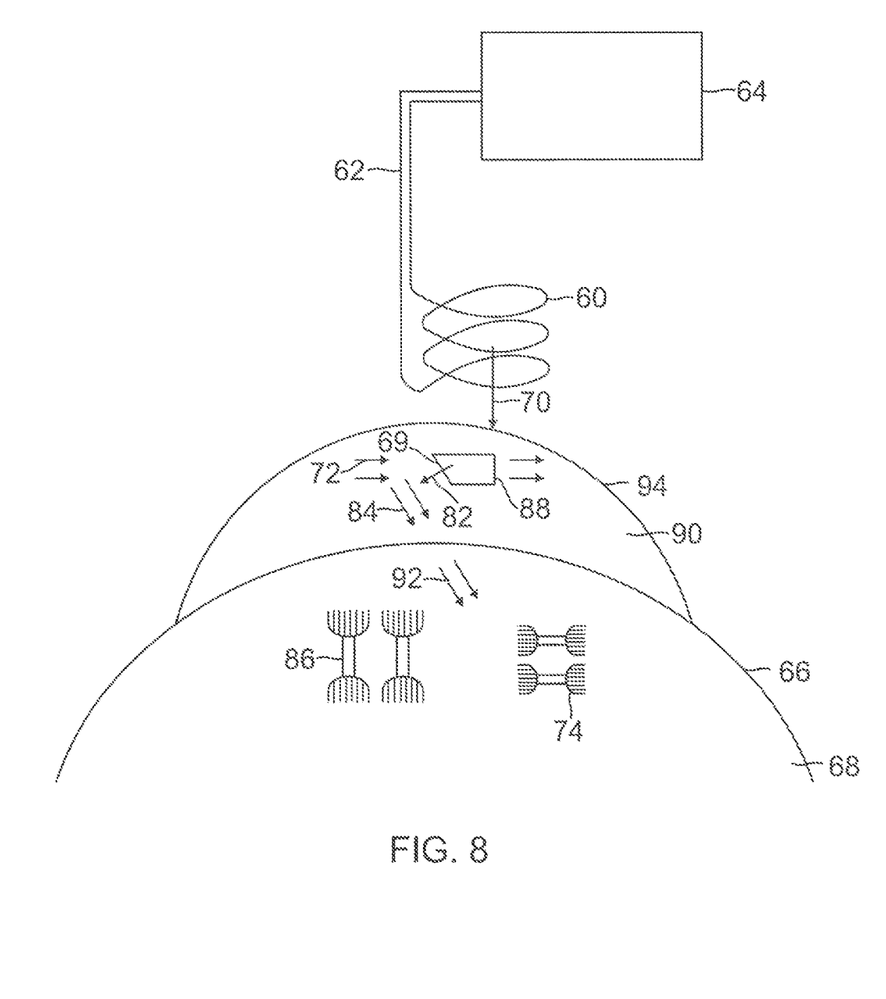
FIG. 8 is a cross-sectional view of an embodiment of the invention, shown in relation to a human head.

FIG. 8 illustrates an embodiment of the invention, which is employed to enhance the effectiveness of TMS for the brain of the human or other animals. In this embodiment, a conductive gel 90 is applied to the scalp to form a continuum of electrical conductivity between the surface of the gel not in contact with the head 66 and the neuronal structures 74 and 86 within the head. Non-conductive solid object 88 is embedded within the gel at a location that is approximately below planar electrical coil 60. In a analogous manner as described for the apparatus in FIG. 7, an electrical current pulse is applied by current source 64 to planar coil 60 to produce magnetic field pulse 70. This pulse induces a voltage and consequent current pulse within the conductive gel and within the head, with the induced current pulse oriented parallel to the plane of coil 60. This pulse can then stimulate polarization activity in neurons 74 which are oriented parallel to the plane of coil 60. The non-conductive solid object serves to divert a portion of induced current pulse 84 into a direction which is not parallel to the plane of the coil, by the mechanism described above. This diverted current will flow across the boundary between the conductive gel and the surface of head into the tissue within the head. Hence a pulse of electrical current 92 will flow within the head, with a component which is oriented perpendicular to the plane of coil 60. This component can then stimulate polarization activity in neurons 86 which are oriented perpendicular to the plane of the coil. In this way, this embodiment of the invention enables the stimulation of neurons within the head oriented in all directions using otherwise conventional TMS equipment.

While the embodiments of the invention described above incorporate simple circular planar electrical coils, any configuration of stimulus coil may be used in conjunction with the embodiments of the invention. Hence, for example, so-called "FIG. 8" planar coils, which produce a more focused magnetic field pulse, may be used. Arrays of planar coils may also be employed in connection with a single non-conductive solid object or a plurality of such objects. Such arrays of cods may be simulated independently of each other. Electrical coils producing gradient magnetic fields and magnetic fields oriented in directions other than perpendicular to the surface of the head may also be employed.

Typical material, which can serve as a gel in the apparatus shown in FIG. 8, is gel used in electroencephalography for electrode attachment. While the embodiment illustrated in FIG. 8 shows the employment of a KEEL to stimulate neurons within a human head, the same principle may be applied to employ a KEEL to stimulate biological cells in other portions of the human body, such as the spine or heart, or in portions of the bodies of other animals. While a single KEEL is described above to illustrate its principle of operation, multiple KEELs or arrays of KEELs may be employed as well. Moreover, KEELs may have specific shapes designed to divert current flow in a manner specific to a given application, such as to stimulate a certain group of neurons within a biologic structure. A KEEL with a shape intended to produce an asymmetric current flow is a further example of an embodiment contemplated here.

While particular embodiments of the present invention have been disclosed, it is to be understood that various different modifications and combinations are possible and are contemplated within the true spirit and scope of the disclosed embodiments. There is no intention, therefore, of limitations to the exact disclosures herein presented.

What is claimed is:

1. An apparatus for applying electrical current to a conductive biologic structure located in an environment, the apparatus comprising:
   a conductive medium configured to cover and contact at least a portion of the biologic structure, the conductive medium being selected from a group consisting of a conductive liquid and a conductive gel, the conductive medium having a first surface separating it from the environment; and
   at least one non-conductive solid object fully immersed within the conductive medium, wherein the non-conductive solid object is positioned between the biologic structure and the first surface, the non-conductive solid object having a surface which is neither parallel nor perpendicular to the first surface of the conductive medium, wherein there is no electrical connection to the non-conductive solid object, wherein the non-conductive solid object is configured to produce a secondary source responsive to a magnetic field produced by an electrical current source conveying electrical current to an electrical coil located external to the conductive medium, and wherein the secondary source applies electrical current to the biologic structure.

2. The apparatus of claim 1, wherein the non-conductive solid object has an elongated shape oriented substantially parallel to the first surface of the conductive medium and a substantially flat end surface, the flat end surface positioned proximate to the biologic structure, wherein the substantially flat surface and the first surface of the conductive medium are at an angle with respect to each other which is between 30 degrees and 60 degrees.

3. The apparatus of claim 1, wherein the non-conductive solid is made from a material selected from the group consisting of glass, quartz, sapphire, diamond, reinforced plastic, and non-reinforced plastic.

4. The apparatus of claim 1, wherein the conductive liquid is a saline solution.

5. The apparatus of claim 1, wherein the at least one non-conductive solid object comprises a plurality of non-conductive solid objects fully immersed within the conductive medium and positioned between the biologic structure and the first surface, each of the non-conductive objects having a surface which is neither parallel nor perpendicular to the first surface of the conductive medium.

6. An apparatus for applying electrical current to a conductive biologic structure, the biologic structure having a surface, the apparatus comprising:
   an electrically-conductive gelatinous material configured to cover and contact a portion of the surface of the biologic structure, said gelatinous material having a thickness and having a surface separating it from the environment, the surface being substantially parallel to the surface of the portion of the biologic structure; and
   a non-conductive solid object fully immersed within the gelatinous material, wherein the non-conductive solid object is positioned between the portion of the surface of the biologic structure and the surface of the gelatinous material, the object having a surface which is neither parallel nor perpendicular to the portion of the surface of the biologic structure, wherein there is no electrical connection to the non-conductive solid object, wherein the non-conductive solid object is configured to produce a secondary source responsive to a magnetic field produced by an electrical current source conveying electrical current to an electrical coil, and wherein the secondary source applies electrical current to the biologic structure.

7. The apparatus of claim 6, wherein the gelatinous material is configured to cover and contact a portion of a head of a human being.

8. The apparatus of claim 6, wherein the gelatinous material is configured to cover and contact a portion of a body of a human being.

9. The apparatus of claim 6, wherein the gelatinous material is configured to cover and contact a portion of an animal.

10. The apparatus of claim 6, wherein the electrically conductive gelatinous material is electroencephalography electrode paste.

11. The apparatus of claim 6, wherein the non-conductive solid is made from a material selected from the group consisting of glass, quartz, sapphire, diamond, reinforced plastic, and non-reinforced plastic.

* * * * *